United States Patent
Zhou et al.

(10) Patent No.: US 12,274,778 B2
(45) Date of Patent: Apr. 15, 2025

(54) PAENIBACILLUS STRAIN CAPABLE OF PRODUCING POLYSACCHARIDES WITH AFTER-SUN REPAIR EFFECT AND USE THEREOF

(71) Applicant: ZHEJIANG UNIVERSITY, Hangzhou (CN)

(72) Inventors: Wenwen Zhou, Hangzhou (CN); Yiqing Wang, Hangzhou (CN)

(73) Assignee: ZHEJIANG UNIVERSITY, Hangzhou (CN)

( * ) Notice: Subject to any disclaimer, the term of this patent is extended or adjusted under 35 U.S.C. 154(b) by 1032 days.

(21) Appl. No.: 16/982,060

(22) PCT Filed: Oct. 18, 2019

(86) PCT No.: PCT/CN2019/111949
§ 371 (c)(1),
(2) Date: Oct. 26, 2021

(87) PCT Pub. No.: WO2020/078467
PCT Pub. Date: Apr. 23, 2020

(65) Prior Publication Data
US 2022/0054390 A1 Feb. 24, 2022

(30) Foreign Application Priority Data
Oct. 18, 2018 (CN) .......................... 201811216217.0

(51) Int. Cl.
*A61K 8/73* (2006.01)
*A61Q 19/00* (2006.01)
*C12N 1/20* (2006.01)
*C12P 19/04* (2006.01)

(52) U.S. Cl.
CPC .............. *A61K 8/73* (2013.01); *A61Q 19/004* (2013.01); *C12N 1/205* (2021.05); *C12P 19/04* (2013.01)

(58) Field of Classification Search
CPC ........ A61K 8/73; A61Q 19/004; C12N 1/205; C12N 1/20; C12P 19/04; C12R 2001/01
See application file for complete search history.

(56) References Cited

FOREIGN PATENT DOCUMENTS

| CN | 101870739 A | 10/2010 | | |
|---|---|---|---|---|
| CN | 109321501 A | 2/2019 | | |
| KR | 20090120347 A | 11/2009 | | |
| TW | 201331369 A | * | 8/2013 | ............. A01N 37/52 |

OTHER PUBLICATIONS

Raza et al., Optimization, purification, characterization and antioxidant activity of an extracellular polysaccharide produced by Paenibacillus polymyxa SQR-21. Bioresource Technology 102 [2011] 6095-6103 (Year: 2011).*
Liu, Zhenhua et al. "Function of Polysaccharides from Paenibacillus Polymyxa in Microbial Pesticide Formulation" Dec. 15, 2011.
Raza, W. et al. "Optimization, purification, characterization and antio xidant activity of an extracellular polysaccharide produced by Paenibacillus polymyxa SQR-21" Feb. 16, 2011.
International Search Report (PCT/CN2019/111949); Date of Mailing: Jan. 22, 2020.

* cited by examiner

*Primary Examiner* — Robert A Wax
*Assistant Examiner* — Ngoc-Anh Thi Nguyen
(74) *Attorney, Agent, or Firm* — Wiersch Law Group

(57) ABSTRACT

The present invention discloses a *Paenibacillus* strain capable of producing polysaccharides with an after-sun repair effect and use thereof. This strain is classified and named as *Paenibacillus polymyxa* PYQ1, preserved in China General Microbiological Culture Collection Center with a preservation number of CGMCC No. 16444. The present invention includes isolation and cultivation of strains and 16S rDNA identification; obtaining extracellular polysaccharides from fermentation product of the strain and use of the extracellular polysaccharides produced by the strains in repairing after-sun damages. The polysaccharides produced by *Paenibacillus* PYQ1 disclosed by the present invention can significantly improve proliferation activity of damaged cells after sun exposure, and has remarkable after-sun damage repairing effect; and as a natural product of microbial fermentation, the polysaccharides have characteristics of a low cost, simple and easy acquisition and the like, can be applied to the preparation of related after-sun repairing agents, and have a good market application prospect.

8 Claims, 2 Drawing Sheets

PAENIBACILLUS STRAIN CAPABLE OF PRODUCING POLYSACCHARIDES WITH AFTER-SUN REPAIR EFFECT AND USE THEREOF

CROSS-REFERENCE TO RELATED APPLICATIONS

This is the United States national phase of International Patent Application No. PCT/CN2019/111949, filed on Oct. 18, 2019, which claims priority to Chinese patent application No. 201811216217.0, filed on Oct. 18, 2018, the entire contents of which are incorporated herein by their references.

TECHNICAL FIELD

The present invention belongs to the field of new strain screening technology and microorganism technology, and in particular, relates to a *Paenibacillus* strain capable of producing polysaccharides with after-sun repair effect and a use thereof.

BACKGROUND

According to different wavelengths, ultraviolet rays can be divided into three categories: UVA with a wavelength of 320-400 nm, UVB with a wavelength of 280-320 nm and UVC with a wavelength of 200-280 nm. The ozone layer located more than ten kilometers above the earth's surface can absorb all UVC and most UVB, which are the most harmful to human skin, and it is the natural barrier of biological activities on the earth. However, with the aggravation of air pollution year by year, the ozone layer has been seriously damaged, and the ultraviolet rays radiated to the earth's surface have increased significantly, affecting people's quality of life. Therefore, the damage of UV to organisms and the protection against it have become a hot issue in the world.

Skin is the first line of defense and biological barrier against various physical and chemical stimuli, and UV is one of the important harmful factors contacting the skin. Studies have shown that excessive exposure to ultraviolet radiation is the main cause of skin photodamage, which can cause erythema, inflammation, pigmentation and so on. In addition, UV may induce cells to produce excessive reactive oxygen species (ROS), destroy their own antioxidant defense system, cause lipid peroxidation, affect related signal transduction pathways, and damage the structures or functions of cells, thus inducing immunosuppression, malignant tumors and other diseases.

It is worth noting that in recent years, the main role of skin care products in maintaining healthy skin is being emphasized. However, at present, the functional components of skin care products in the market with after-sun repair effect are mostly chemicals or natural plant extracts. Natural extracts from microorganisms are becoming a new upstart in this field. Compared to the chemicals, natural extracts are preferred by consumers. Natural extracts from microorganisms are with lower production cost and easier to obtain than those from plants, and therefore have a good market prospect.

SUMMARY

The purpose of the present invention is to provide a strain capable of producing polysaccharides for after-sun damage repair and an application method thereof, providing low-cost and highly accessible materials derived from microbial fermentation, which are different from chemicals and plant extracts, and thus have a broad application prospect.

The present invention discloses a microbial strain capable of producing polysaccharides which have protective effects against UV-induced damage by promoting the proliferation of damaged cells. The strain is purple by Gram's staining, and it is a Gram-positive bacterium. At the same time, the strain has been identified by determining the sequence of 16S rDNA. The measured sequence of the strain was analyzed with comparison by BLAST in the NCBI database, and it was found that the 16S rDNA sequences of the strain was highly homologous with those of *Paenibacillus polymyxa*. It can be confirmed that the strain is *Paenibacillus polymyxa*, named as *Paenibacillus polymyxa* PYQ1. The biological preservation information of this strain is: China General Microbiological Culture Collection Center (Address: No. 1, Beichen West Road, Chaoyang District, Beijing), the strain preservation number is CGMCC No. 16444, and the preservation date is Sep. 10, 2018.

The single colony of the strain in an agar medium for polysaccharide production is round, white and viscous.

The present invention provides a method for obtaining extracellular polysaccharides produced by fermentation of the strain, including:

Step 1 of growing *Paenibacillus polymyxa* PYQ1 on an agar medium for polysaccharide production, picking the *Paenibacillus* strain and inoculating the *Paenibacillus* strain to a liquid fermentation medium for polysaccharide production to be shake-cultured in a shaker at 30-37° C. for 24-48 h; and Step 2 of centrifuging the resulted fermentation broth to remove bacteria to obtain a supernatant, deproteinizing the supernatant for 4-6 times, and adding absolute ethanol to precipitate polysaccharides; redissolving and dialyzing the precipitated polysaccharides to remove small molecules, and then performing freeze-drying to obtain the polysaccharides.

Preferably, a rotating speed of the shaker is 150 rpm, and in the step 2, a fermentation broth is centrifuged at 4000 g for 10 min to remove bacteria to obtain a supernatant. The supernatant is deproteinized by a Sevag method, and absolute ethanol of 3 times a volume of the supernatant is added to precipitate polysaccharides.

Preferably, the agar medium for polysaccharide production includes components of: 10-20 g/L of sucrose, 5-10 g/L of tryptone, 5 g/L of yeast powder, 3 g/L of $Na_2HPO_4 \cdot 12H_2O$, 15-20 g/L of agar, and a balance of distilled water.

Preferably, the liquid fermentation medium for polysaccharide production includes components of: 50 g/L of sucrose, 5 g/L of tryptone, 1 g/L of yeast powder, 3 g/L of $Na_2HPO_4 \cdot 12H_2O$, and a balance of distilled water.

The present invention also provides a use of the polysaccharides as an after-sun damage repairing agent. A polysaccharide solution sterilized by membrane sterilization is added into skin care products. After UV damage to human skin, skin care products containing the polysaccharides are applied on the skin surface to achieve the effect of after-sun repair. The concentration of the polysaccharides in the skin care product is 100 μg/mL-1000 μg/mL.

The after-sun repair efficacy of the polysaccharide solution can be tested by an MTT assay of human immortalized epidermal keratinocytes (HaCaT cells).

The strain provided by the present invention can be fermented on a liquid fermentation medium for polysaccharide production to produce a large amount of polysaccharides, and the produced polysaccharides can effectively repair damage after sun exposure. In addition, as a microbial fermentation product, compared with chemicals and plant extracts commonly used in the field of after-sun repair, it has the advantages of easily available active ingredients and a low price.

DESCRIPTION OF EMBODIMENTS

Embodiments of the present invention will be described in detail below, but the following embodiments are not intended to limit the scope of protection of the present invention.

Figure 1:
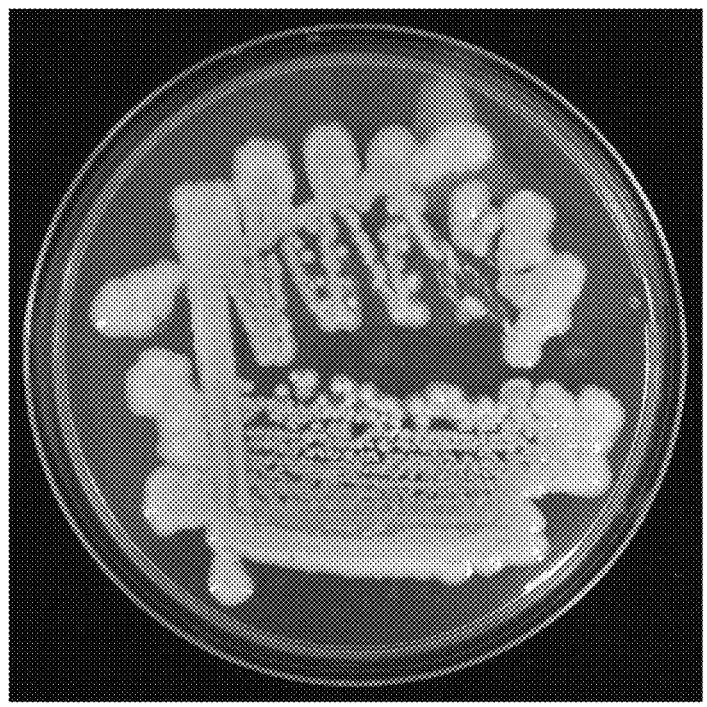
FIG. 1 shows the colony characteristics of the PYQ1 strain of the present invention on the solid plate.

Embodiment 1: Extraction and Content Determination of Extracellular Polysaccharides Produced by the Above-Mentioned Strains The colony of the strain was picked from the agar medium for polysaccharide production and inoculated into the liquid fermentation medium for polysaccharide production. A fermentation broth was obtained by shaking culture in a shaker at 30° C. and 150 rpm for 48 hours. FIG. 1 shows the colony characteristics of the PYQ1 strain on the solid plate.

The components of the agar medium for polysaccharide production include: 20 g/L of sucrose, 10 g/L of tryptone, 5 g/L of yeast powder, 3 g/L of $Na_2HPO_4.12H_2O$, 20 g/L of agar, and a balance of distilled water. The components of the liquid fermentation medium for polysaccharide production include: 50 g/L of sucrose, 5 g/L of tryptone, 1 g/L of yeast powder, 3 g/L of $Na_2HPO_4.12H_2O$, and a balance of distilled water.

The fermentation broth was centrifuged at 4000 g for 10 min to remove bacteria to obtain a supernatant. A Sevag solution (n-butanol:chloroform=1:4) of ¼ the volume of the supernatant was added to the supernatant, shaken for 15 min, and then centrifuged at 4000 g for 10 min to remove denatured proteins at the interface. After repeating for 5 times, the upper liquid was taken, absolute ethanol of 3 times the volume was added to precipitate polysaccharides. After redissolving, the precipitated polysaccharide was dialyzed with a 3500 D dialysis bag to remove small molecules. After dialysis, the polysaccharide solution was concentrated under a reduced pressure and then freeze-dried, to obtain extracellular polysaccharides produced by fermentation of the strain.

The yield of the extracellular polysaccharides produced by the strain PYQ1 was 10.14 g/L as measured by a phenol-sulfuric acid method.

Embodiment 2: Identification of the Microbial Strain of the Present Invention

Figure 2:
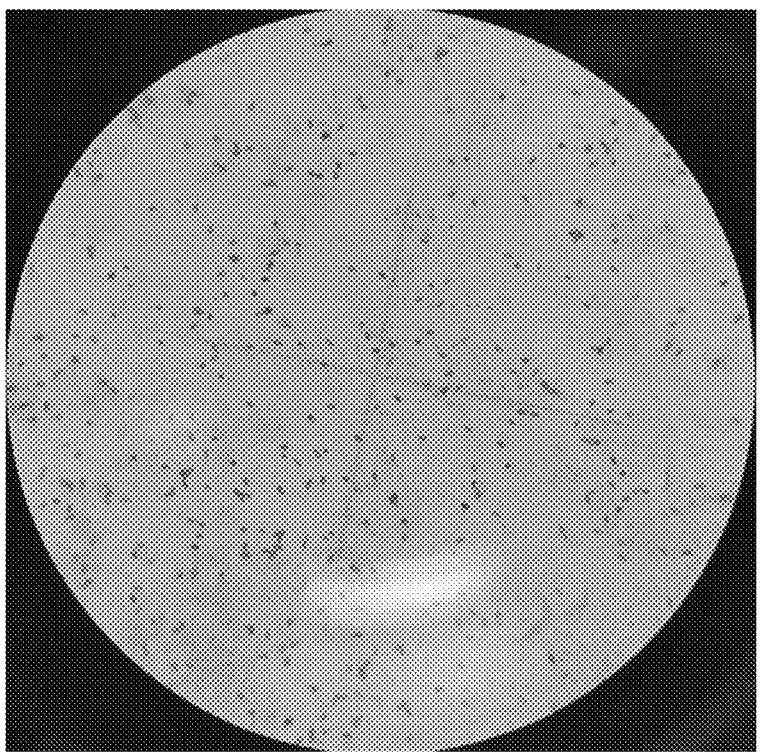
FIG. 2 shows the Gram's staining result of the PYQ1 strain of the present invention.

As shown in FIG. 2, the strain is purple by Gram's staining, and is a Gram-positive bacterium. According to the steps of Takara Bacteria Genomic DNA Extraction Kit, the total DNA of the strain was extracted, the 16S rDNA gene of the strain was amplified with universal primers 27F and 1492R, the amplified product was recovered and sequenced, and the strain was identified by determining the sequence of 16S rDNA. The obtained sequence results were aligned by BLAST in NCBI, and the recognized standard sequence data homologous to 16S rDNA of the strain was obtained from the GenBank database. The sequence similarity was calculated by MEGA software, and phylogenetic analysis was performed by the Neighbor-Joining algorithm.

Figure 3:
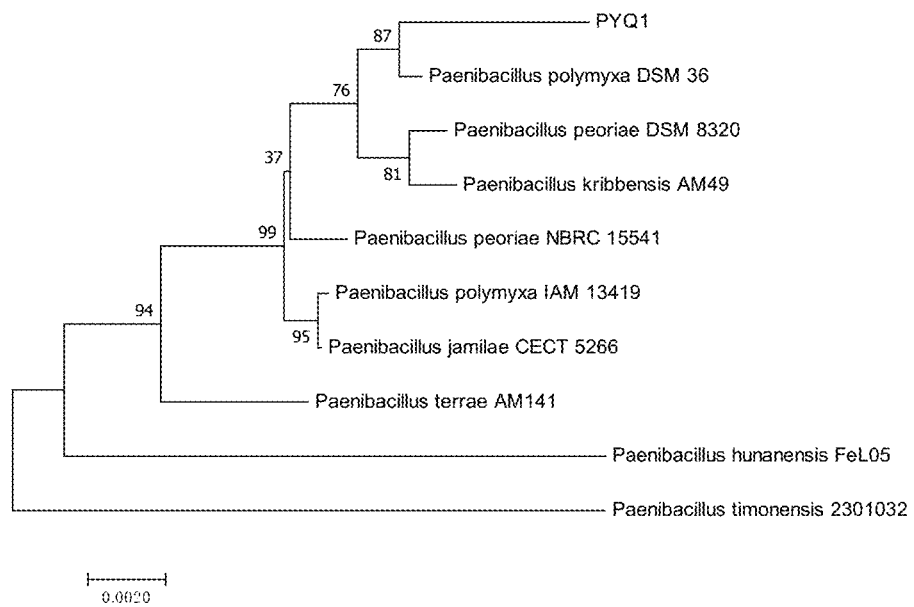
FIG. 3 shows a Neighbor-Joining phylogenetic tree of 16S rDNA sequence of the PYQ1 strain of the present invention.

The constructed phylogenetic tree of the strain is shown in FIG. 3, which has the highest homology with *Paenibacillus polymyxa*. It was confirmed that the strain of the present invention is *Paenibacillus polymyxa* and named *Paenibacillus polymyxa* PYQ1.

Embodiment 3: Use of the Above Polysaccharides as an After-Sun Damage Repair Agent HaCaT cells in a logarithmic phase were collected and inoculated in 96-well plates, 5000 cells per well, and cultured in 5% $CO_2$ incubator at 37° C. The cells were divided into a control group, a UV model group, a polysaccharide group (1 mg/mL), an octocrylene group (8%) and a Vc group (1 mg/mL). The last two groups were positive controls, and 3 wells were repeated for each group. After 24 hours of cell culture, the culture medium was changed into a phosphate buffer solution (PBS) and irradiated with UV, while the control group was covered with foil paper to avoid light. The PBS was sucked out and a culture medium was added. The culture medium of the polysaccharide group contained 1 mg/mL of the extracellular polysaccharides produced by the above stain, the culture medium of the octocrylene group contained 8% 2-ethylhexyl 2-cyano-3,3-diphenylacrylate, and the culture medium of the Vc group contained 1 mg/mL of Vc. After continuing to culture in the incubator for 24 hours, an MTT assay was used to detect the cell viability after the UV irradiation, and to evaluate whether the cell proliferation activity is increased after the action of the after-sun repair composition.

The MTT assay is a method to detect the survival and growth of cells. The detection principle is that succinate dehydrogenase in mitochondria of living cells can reduce exogenous MTT into water-insoluble blue-purple crystalline formazan and deposit it in cells, while dead cells have no such function. Dimethyl sulfoxide (DMSO) can dissolve formazan in cells, and its light absorption value is measured by a microplate reader at 490 nm or 570 nm, which can indirectly reflect the number of living cells.

Cell survival rate (%)=the OD value of experimental well/the OD value of control well×100%

Figure 4:
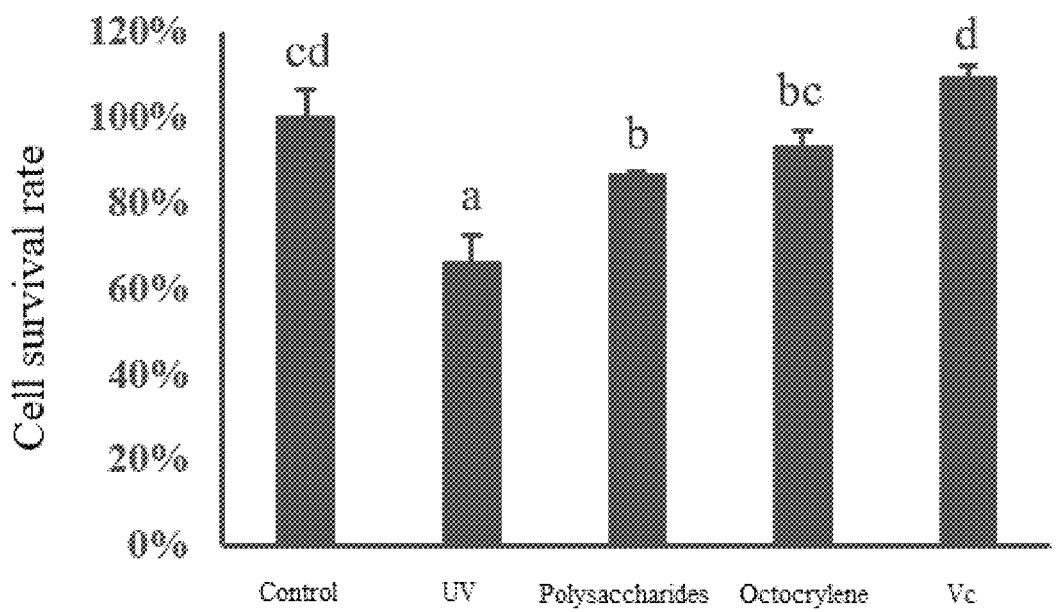
FIG. 4 shows the protective effect of polysaccharides produced by fermentation of the PYQ1 strain on HaCaT.

According to FIG. 4, the survival rate of HaCaT cells under UV treatment was greatly reduced, which was only 65.97% of the control group, but the polysaccharide treatment group could significantly improve the survival rate of HaCaT cells after UV irradiation to 86.58%. The results indicated that the extracellular polysaccharides produced by the above strain have remarkable effect of repairing after-sun damages.

What is claimed is:
1. A *Paenibacillus* strain capable of producing polysaccharides with an after-sun repair effect, wherein the *Paenibacillus* strain is preserved in China General Microbiological Culture Collection Center with a preservation name of

*Paenibacillus polymyxa* PYQ1, a preservation number of CGMCC No. 16444 and a preservation date of Sep. 10, 2018.

2. The *Paenibacillus* strain according to claim 1, wherein a single colony of the *Paenibacillus polymyxa* PYQ1 on an agar medium for polysaccharide production is round, white and viscous, wherein the agar medium for polysaccharide production comprises components of: 10-20 g/L of sucrose, 5-10 g/L of tryptone, 5 g/L of yeast powder, 3 g/L of $Na_2HPO_4 \cdot 12H_2O$, 15-20 g/L of agar, and a balance of distilled water; and the *Paenibacillus polymyxa* PYQ1 is capable of producing a large amount of extracellular polysaccharides in a liquid fermentation medium for polysaccharide production, wherein the liquid fermentation medium for polysaccharide production comprises components of: 50 g/L of sucrose, 5 g/L of tryptone, 1 g/L of yeast powder, 3 g/L of $Na_2HPO_4 \cdot 12H_2O$, and a balance of distilled water.

3. A method for preparing polysaccharides based on the *Paenibacillus* strain according to claim 1, comprising:
   step 1 of growing *Paenibacillus polymyxa* PYQ1 on an agar medium for polysaccharide production, picking the *Paenibacillus* strain and inoculating the *Paenibacillus* strain to a liquid fermentation medium for polysaccharide production to be shake-cultured in a shaker at 30-37° C. for 24-48 h; and
   step 2 of centrifuging the resulted fermentation broth to remove bacteria to obtain a supernatant, deproteinizing the supernatant for 4-6 times, and adding absolute ethanol to precipitate polysaccharides; redissolving and dialyzing the precipitated polysaccharides to remove small molecules, and then performing freeze-drying to obtain the polysaccharides.

4. The method accord to claim 3, wherein the deproteinizing is performed by a Sevag method, which comprises: preparing a Sevag solution of n-butanol and chloroform in a ratio of 1:4 (V/V) of n-butanol to chloroform, adding the Sevag solution of ¼ a volume of the supernatant into the supernatant, vigorously shaking for 15 min to fully denature proteins, and centrifuging for 10 min at 4000 g to remove denatured proteins at an interface.

5. The method accord to claim 3, wherein the dialyzing is performed with a 3500 D dialysis bag, and comprises first dialyzing with running water for 24 h, dialyzing with distilled water for 48 h, and replacing the distilled water every 8 h.

6. A skin care product for repairing after-sun damages, comprising the polysaccharides prepared by the method according to claim 3 as an additive.

7. The skin care product according to claim 6, wherein the skin care product is applied to a damaged skin within 0-4 h after a UV damage.

8. The skin care product according to claim 7, wherein the polysaccharides are added into the skin care product in an amount of 100 µg/mL-1000 µg/mL.

\* \* \* \* \*